US00PP13221P2

(12) United States Plant Patent
Smith

(10) Patent No.: US PP13,221 P2
(45) Date of Patent: Nov. 12, 2002

(54) CHRYSANTHEMUM PLANT NAMED 'SPICY YOCHERYL'

(75) Inventor: Mark Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 21 days.

(21) Appl. No.: 09/837,584

(22) Filed: Apr. 19, 2001

(51) Int. Cl.[7] ..... A01H 5/00
(52) U.S. Cl. ..... Plt./290
(58) Field of Search ..... Plt./287, 290

(56) References Cited

U.S. PATENT DOCUMENTS 4,616,099 A * 10/1986 Sparkes ..... 47/58

OTHER PUBLICATIONS

Shukla, et al., 1993, "Mutation Studies on Early and Late Varieties of Garden Chrysanthemums", J. Nucleic Agric. Biol., 22 (3–4):138–142.*

Broetjes, et al., 1980, "A Mutant of a Mutant of a . . . Irradiation of Progressive Radiation Induced Mutants in a Mutation Breeding Programme with *Chrysanthimum morifolium*", Euphytica, 29:525–530.*

Gosling, ed., 1979, "The Chrysanthemum Manual—6$^{th}$ Edition", The National Chrysanthemum Society, London, Essex Telegraph Press, Ltd., pp. 329–336.*

Broetjes, et al., 1978, "Application of Mutation Breeding Methods in the Improvement of Vegetatively Propagated Crops", Elsevier Sci. Pub. Co., New York, pp. 162–175.*

Searle, et al., 1968, "Chrysanthemums the Year Round", Blanford Press, London, pp. 27–29, 320–327.*

Chan, 1966, "Chrysanthemum and Rose Mutations Induced by X–rays" Am. Soc. Hort. Sci. Proc., pp. 613–620.*

Broertjes, 1966, "Mutation Breeding of Chrysanthemums", Euphytica, 15:156–162.*

Dowrick, et al., 1966, "The Induction of Mutations in Chrysanthemum Using X– and Gamma Radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Spicy Yocheryl', characterized by its upright plant habit; freely branching growth habit; uniform and freely flowering habit; decorative-type inflorescences; and dark bronze ray florets.

1 Drawing Sheet

BACKGROUND OF THE INVENTION

The present invention relates to a new and distinct cultivar of Chrysanthemum plant, botanically known as *Chrysanthemum×morifolium* and hereinafter referred to by the name 'Spicy Yocheryl'.

The new cultivar is a product of a planned breeding program conducted by the Inventor in Fort Myers, Fla. The objective of the breeding program is to create new garden-type Chrysanthemum cultivars having inflorescences with desirable inflorescence forms, attractive floret colors and good garden performance.

The new Chrysanthemum is a naturally-occurring whole plant mutation of a proprietary induced mutation that originated by exposing unrooted cuttings of the Chrysanthemum cultivar Yocheryl, disclosed in U.S. Plant Pat. No. 11,846, to X-ray radiation in July, 1998, in Fort Myers, Fla. The new Chrysanthemum was discovered and selected by the Inventor as a single flowering plant within a population of flowering plants of the irradiated selection in January, 1999 in a controlled environment in Fort Myers, Fla. The selection of this plant was based on its desirable inflorescence form, attractive ray floret color and good garden performance.

Asexual reproduction of the new cultivar by terminal cuttings taken in a controlled environment in Fort Myers, Fla. since March, 1999, has shown that the unique features of this new Chrysanthemum are stable and reproduced true to type in successive generations.

SUMMARY OF THE INVENTION

The cultivar Spicy Yocheryl has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Spicy Yocheryl'. These characteristics in combination distinguish 'Spicy Yocheryl' as a new and distinct cultivar:

1. Upright plant habit.
2. Freely branching, dense, full plants.
3. Uniform and freely flowering.
4. Decorative-type inflorescences.
5. Dark bronze-colored ray florets.

Compared to plants of the cultivar Yocheryl, plants of the new Chrysanthemum flower slightly earlier and differ in ray floret color.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Spicy Yocheryl'.

The photograph at the bottom of the sheet comprises a close-up view of typical inflorescences of the cultivar 'Spicy Yocheryl'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One rooted cutting was planted in a 15-cm container in July, 2000 and plants were grown under natural season conditions. Plants were not pinched, that is, the terminal apex was not removed to enhance branching. Measurements and numerical values represent averages for typical flowering plants.

Botanical classification: *Chrysanthemum×morifolium* cultivar Spicy Yocheryl.

Commercial classification: Decorative-type garden Chrysanthemum.

Parentage: Naturally-occurring whole plant mutation of a proprietary *Chrysanthemum×morifolium* induced mutation, not patented.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous decorative-type garden Chrysanthemum. Inverted triangle; upright plant form. Stems initially upright, then slightly outwardly spreading giving a uniformly flat-top appearance to the plant. Freely branching with about 9 lateral branches per plant.

*Plant height.*—About 24 cm.

*Plant diameter.*—About 31.5 cm.

*Lateral branches.*—Length: About 20 cm. Diameter: About 5.5 mm. Internode length: About 1.75 cm. Aspect: Mostly upright. Texture: Pubescent. Color: 146A with anthocyanin, close to 187A, at nodes.

*Foliage description.*—Leaf arrangement: Alternate. Length: About 5.6 cm. Width: About 3.5 cm. Apex: Cuspidate to mucronate. Base: Attenuate to truncate. Margin: Palmately lobed, sinuses mostly divergent. Texture: Both surfaces, pubescent; veins prominent on lower surface. Color: Young foliage upper surface: 147A. Young foliage lower surface: Darker than 147B. Mature foliage upper surface: 147A. Mature foliage lower surface: 147B. Venation upper surface: 147A. Venation lower surface: 147B. Petiole length: About 1.6 cm. Petiole diameter: About 2 mm. Petiole, color, both surfaces: 146C.

Inflorescence description:

*Appearance.*—Decorative-type inflorescence form with elongated oblong-shaped ray florets. Inflorescences borne on terminals above foliage, arising from leaf axils. Disk and ray florets arranged acropetally on a capitulum. About 9 inflorescences per lateral; about 81 inflorescences per plant.

*Flowering response.*—Under natural season conditions, plants flower in mid-October in the Nothern Hemisphere and continue to flower for at least three weeks depending on weather conditions.

*Inflorescence bud (before showing color).*—Height: About 4 mm. Diameter: About 7 mm. Phyllary color: 143A to 146A.

*Inflorescence size.*—Diameter: About 4.7 cm. Depth (height): About 1.8 cm. Disc diameter: About 2 mm or less, inconspicuous. Receptacle diameter: About 5 mm.

*Ray florets.*—Shape: Elongated oblong to somewhat spatulate. Length: About 2.3 cm. Corolla tube length: About 5 mm. Width: About 8 mm. Apex: Acute to rounded. Margin: Entire. Texture: Smooth, glabrous, satiny. Orientation: Intially upright and incurved, then perpendicular to the peduncle and concave. Number of ray florets per inflorescence: About 235. Color: When opening and fully opened, upper surface: 9A to 12A overlain with 45A to 46A; towards margins and apex, more heavily overlain with 45A to 46A. Overall tonality, more red and richer than 167A. With subsequent development, red overtones become less prominent. When opening and fully opened, lower surface: 9B to 9C underlain with 59A; towards center and apex, more heavily overlain with 59A. Overall tonality, more red than 167A, dulled. With subsequent development, red undertones become less prominent.

*Disc florets.*—Shape: Tubular, apex dentate. Length: About 6 mm. Width: Apex: About 2 mm. Base: About 1 mm. Number of disc florets per inflorescence: Less than 20. Color: Immature: 154A. Mature: Apex: 9A. Mid-section: 154D. Base: 155D.

*Peduncle.*—Aspect: Flexible, angled about 45° from the stem. Length: First peduncle: About 6.4 cm. Fourth peduncle: About 8.8 cm. Diameter: About 2 mm. Texture: Pubescent. Color: 146A.

*Reproductive organs.*—Androecium: Present on disc florets only. Anther color: 9A to 12A. Pollen: Moderate. Pollen color: 12A. Gynoecium: Present on both ray and disc florets.

*Seed.*—Seed production has not been observed.

Disease resistance: Plants of the new Chrysanthemum have not been shown to be resistant to pathogens common to Chrysanthemums.

Garden performance: Plants of the new Chrysanthemum have been observed to be tolerant to rain and wind.

It is claimed:

1. A new and distinct cultivar of Chrysanthemum plant named 'Spicy Yocheryl', as illustrated and described.

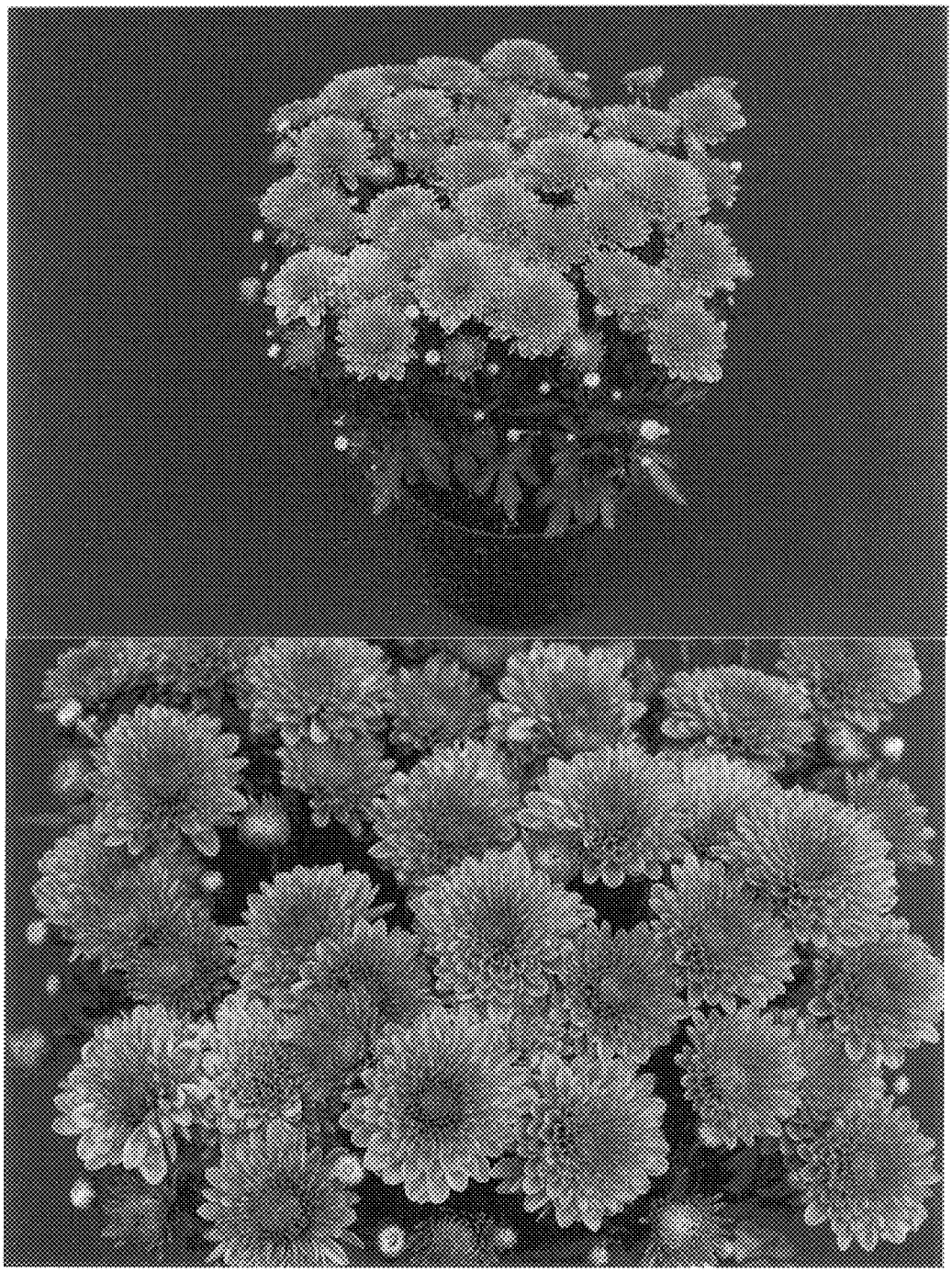

* * * * *